United States Patent [19]

Olsson et al.

[11] Patent Number: 4,905,685

[45] Date of Patent: Mar. 6, 1990

[54] INHALATION ANAESTHESIA EQUIPMENT

[75] Inventors: Sven-Gunnar Olsson, Arloev; Goeran Rydgren, Malmo, both of Sweden

[73] Assignee: Siemens Aktiengesellschaft, Berlin and Munich, Fed. Rep. of Germany

[21] Appl. No.: 180,968

[22] Filed: Apr. 13, 1988

[30] Foreign Application Priority Data

Apr. 14, 1987 [DE] Fed. Rep. of Germany ....... 3712598

[51] Int. Cl.⁴ .................. A61M 16/00; A62B 7/00; A62B 7/02; A62B 7/10
[52] U.S. Cl. .................. 128/203.12; 128/204.18; 128/204.21; 128/205.12.205.27
[58] Field of Search .............. 128/203.14, 203.25, 128/203.28, 204.21, 204.22, 205.11, 205.12, 205.17, 205.18, 205.27, 205.28, 205.29, 203.12, 205.13, 204.18, 205.14, 205.15

[56] References Cited

U.S. PATENT DOCUMENTS

| | | | |
|---|---|---|---|
| 1,567,868 | 12/1925 | Schroder | 128/203.12 |
| 3,200,816 | 8/1965 | Bartlett, Jr. | 128/205.13 |
| 3,283,754 | 11/1966 | Goodner | 128/205.14 |
| 3,378,005 | 4/1968 | Smith, Jr. | 128/205.13 |
| 3,465,753 | 9/1969 | Levy et al. | 128/203.14 |
| 3,592,191 | 7/1971 | Jackson | 128/203.28 |
| 3,741,208 | 6/1973 | Jonsson et al. | 128/204.21 |
| 3,923,053 | 12/1975 | Jansson | 128/205.13 |
| 4,034,753 | 7/1977 | Connel | 128/203.19 |
| 4,127,121 | 1/1978 | Westenkow et al. | 128/203.14 |
| 4,150,670 | 4/1979 | Jewett et al. | 128/204.22 |
| 4,151,843 | 5/1979 | Brekke et al. | 128/205.13 |
| 4,340,044 | 7/1982 | Levy et al. | 128/205.11 |
| 4,611,590 | 9/1986 | Ryschka et al. | 128/203.14 |
| 4,622,976 | 11/1986 | Timpe et al. | 128/203.14 |
| 4,651,729 | 3/1987 | Rae | 128/203.28 |
| 4,702,241 | 10/1987 | Gravenstein et al. | 128/205.12 |
| 4,770,168 | 9/1988 | Rusz et al. | 128/203.14 |
| 4,791,922 | 12/1988 | Lindsay-Scott et al. | 128/205.28 |

FOREIGN PATENT DOCUMENTS

| | | |
|---|---|---|
| 0121255 | 10/1984 | European Pat. Off. . |
| 576139 | 4/1933 | Fed. Rep. of Germany . |
| OS2942623 | 4/1981 | Fed. Rep. of Germany . |
| OS2945472 | 12/1982 | Fed. Rep. of Germany . |
| 1043855 | 11/1953 | France . |
| 798561 | 7/1958 | United Kingdom ........... 128/203.14 |

*Primary Examiner*—Edgar S. Burr
*Assistant Examiner*—Kimberly L. Asher

[57] ABSTRACT

Equipment for administering gaseous anesthetic to a patient has at least one anesthetic reservoir serving as the originating source for anesthetic and a ventilator to which the gas is supplied from the reservoir, the ventilator being in communication with the breathing passages of a patient. To maintain the consumption of anesthetic gas as low as possible and to also assure that the patient is constantly ventilated with fresh anesthetic gas having a defined consumption, the exhalation gas from the patient is fed back to the originating anesthetic source via at least one filter in which predetermined gas components, such as water vapor and carbon dioxide are filtered out. The exhalation gas may be returned to the originating source either directly or through a compressor.

27 Claims, 1 Drawing Sheet

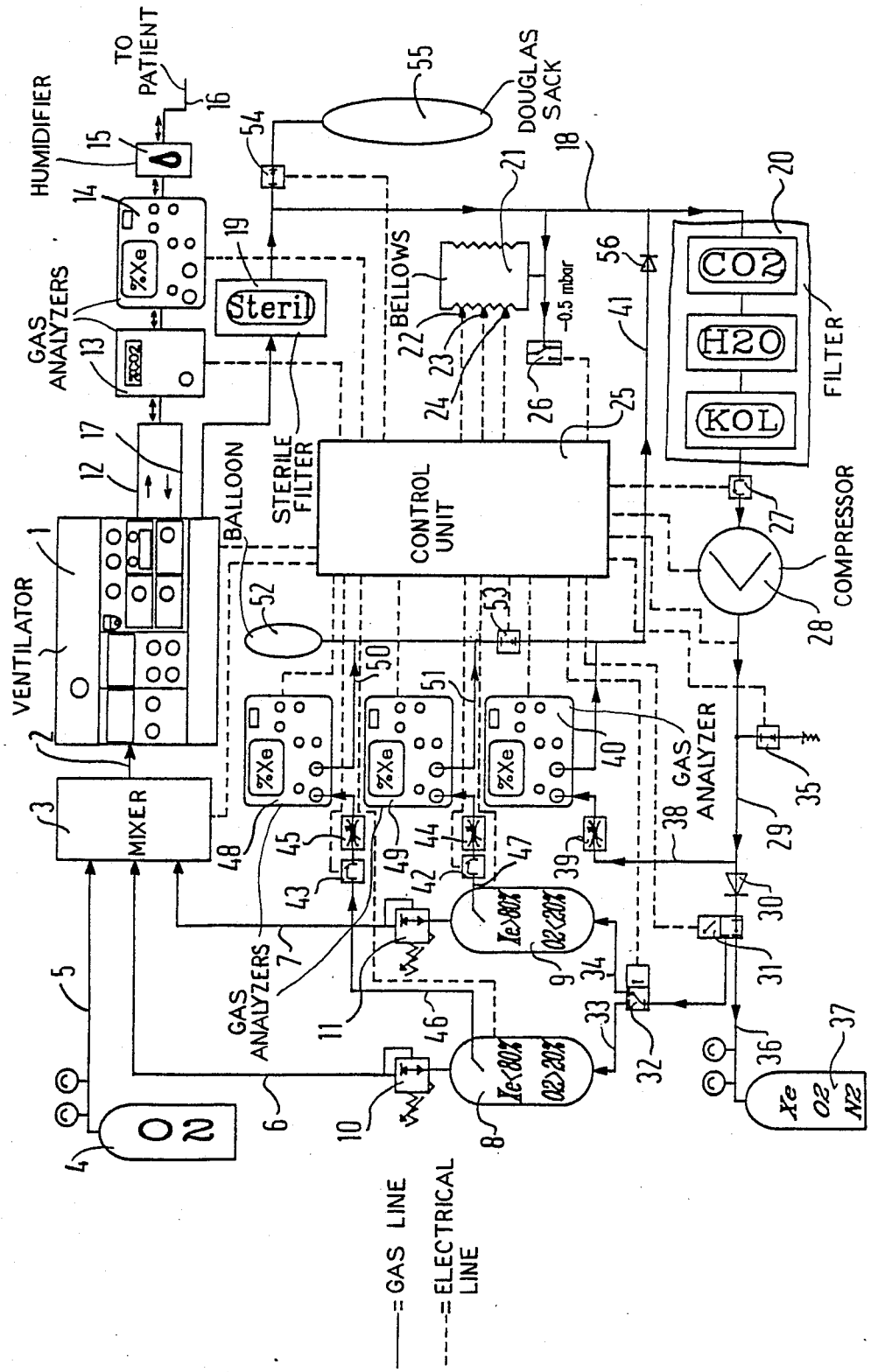

INHALATION ANAESTHESIA EQUIPMENT

BACKGROUND OF THE INVENTION

1. Field of the Invention

The present invention is directed to equipment for administering gaseous anesthetic to a patient by means of a ventilator having an anesthetic reservoir connected thereto.

2. Description of the Prior Art

Inhalation anesthesia equipment having a closed circulation system is described, for example, in European Patent Application 0 121 255. To reduce consumption of anesthetic, the exhaled gas is re-supplied to the inspiration line leading to the patient. This occurs via a carbon dioxide absorber. Used oxygen and anesthetic gas can be added via additional lines. A carbon dioxide analyzer and an oxygen analyzer are connected to the expiration line for monitoring.

A similar anesthesia-ventilation system is disclosed in German Patent 29 45 472. In this system, the exhalation gas is collected in a bellows and mixed with fresh anesthetic gas. During the next inspiration phase, the gas mixture is conducted from the bellows to the patient via a carbon dioxide absorber. Any excess of fresh antesthetic gas is discharged into the environment via a valve.

Another inhalation anesthesia system is described in German OS 29 42 623, which also has a closed circulation path wherein fresh anesthetic gas is continuously supplied. In contrast to German OS 29 45 472, the excess gas is collected in a gas evacuator. From this gas evacuator, the gas can be forwarded to a separator in which the anesthetic can be reclaimed. Polluting the environment with anesthetic gas is thus avoided by collecting the excess gas.

A pulmonary ventilator is described in U.S. Pat. No. 3,741,208 which can be used as an inhalation anesthesia system having closed circulation. The pulmonary ventilator described therein is suitable for use as the ventilator in the equipment disclosed and claimed in the present application. U.S. Pat. No. 3,741,208 also teaches returning the exhalation gas to the inspiration line via a compressor, given a closed system, after undesired gas components such as carbon dioxide have been filtered out, and consumed gas components, such as oxygen, have been added.

All of the above known closed circulation inhalation anesthesia devices have in common supplying anesthetic gas, i.e., a mixture of anesthetic and oxygen, to the patient via an inspiration line, and re-supplying the exhalation gas to the inspiration line via filters. Consumed gas may be replaced, and excess gas may be eliminated to the environment, or may be discharged into a recovery system in these known devices. The composition of the gas mixture in the inspiration line, however, is not reliably determined in any of these known systems. With the exception of the system described in European Application 0 121 255, all of the systems operate with an excess of fresh anesthetic gas. There is no monitoring of the consumption of anesthetic gas in these systems. The loss in volume during a breath is measured using a spirometer in the system described in European Application 0 121 255, and using this value the measured oxygen concentration of the anesthetic gas consumption is calculated therefrom, however, the composition of the gas in the inspiration line is not known, or is at least uncertain. In all of the above systems, the carbon dioxide absorber is disposed in the inspiration line, or immediately therebefore. The function of this absorber is not monitored at all, so that uncleaned gas would be returned to the patient given a saturation, or given a malfunction in this absorber.

SUMMARY OF THE INVENTION

It is an object of the present invention to provide an inhalation anesthesia system which operates with a minimum consumption of anesthetic which nonetheless assures in a simple manner that the patient is constantly quasi-ventilated with fresh anesthetic gas having a defined composition.

Another object of the present invention is to provide such a system wherein administration of the anesthesia can be continued without interruption, even given temporary failure of the filters, or of the return of the exhaled gas.

Another object of the present invention is to provide such a system which reliably prevents ventilation of the patient with pure anesthetic for long times.

Another object of the invention is to provide such a system which does not require additional, compressible volume.

The above objects are achieved in accordance with the principles of the present invention wherein a reservoir serving as the originating source for anesthetic is provided, the anesthetic being supplied to the lungs of a patient from the reservoir through a ventilator, with other gases such as oxygen being added as needed. As noted above, a ventilator as described in U.S. Pat. No. 3,741,208 is suitable for use in the system disclosed herein. The invention, however, is independent of the type of ventilation equipment which is used. It is only necessary that the desired gas mixture is supplied to the lungs of the patient, and is removed from the lungs with the assistance of such equipment.

Further in accordance with the principles of the present invention, the exhalation gas is returned to the originating source via at least one filter in which predetermined gas components, such as carbon dioxide or water, are filtered out. In contrast to conventional systems, however, the exhaled gas is not directly re-supplied to the patient. In the subject matter disclosed herein, the patient is supplied with a defined composition of fresh anesthetic gas from the reservoir. Preferably, the reservoir is of such a size that at least the amount of anesthetic required for maintaining the patient under anesthesia for the desired amount of time is contained therein. Substantially pure, fresh anesthetic gas is present after the exhalation gas is cleaned by the filter, and this can again be returned to the reservoir. If the reservoir contains pure anesthetic at the beginning of anesthesia administration, oxygen is added thereto, for example, in a mixer or directly in the inspiration line. The reservoir may contain the anesthetic in gaseous form, however, it is also possible to provide the anesthetic in liquid form and to supply the liquid anesthetic to the ventilator and to the breathing passages via an evaporator. In this case, a condenser must then be provided in the return line.

Loss of anesthetic can be limited to such an extent with the equipment disclosed herein that substantially only the gas metabolized in the patient, or diffused through the skin, need be replaced. In addition to minimizing such loss of anesthetic, the supply of fresh anesthetic gas is also limited to a minimum, i.e., it is not necessary to supply an excess of anesthetic in the system disclosed herein, in contrast to conventional systems. The system disclosed herein therefore permits the use of an expensive anesthetic, such as xenon, which would be costprohibitive in conventional systems.

A further advantage of the system disclosed herein is that, regardless of the anesthetic employed, extraction of excess gas to a large collecting vessel outside of the treatment room can be eliminated.

Different volumes of supplied fresh anesthetic gas can also be quickly set without difficulty. Even anesthetic gases temporarily dissolve in the body of the patient, insofar as they are later exhaled, can be re-supplied to the system, and are not lost. The anesthetic gases returned to the reservoir can subsequently be re-used.

In one embodiment of the invention, the reservoir contains a gas mixture consisting of an anesthetic and another gas, preferably oxygen. This gas mixture can be directly supplied to the breathing passages via the ventilator.

As noted above, the most significant advantage of the inhalation anesthesia equipment disclosed herein is that the consumption of anesthetic is limited to an absolute minimum, and the anesthetic contained in the exhalation gas is directly resupplied to the reservoir. Even if the filters were to malfunction, anesthesia administration can be continued unimpeded, while corrective measures for eliminating the malfunction are undertaken. Even if a portion of poorly cleaned exhalation gas were to flow back to the reservoir, this would be so highly diluted in the overall volume that the anesthetic gas supplied to the patient would be barely changed in composition.

For this purpose, in a further embodiment of the invention a gas analyzer is provided at least between the filter and the reservoir. This gas analyzer monitors the composition of the gas in this line, and triggers at least one alarm upon the first indication of a deviation in the gas composition. The output signal of this gas analyzer can be directly used to suppress return of the gas to the reservoir such as, for example, by conducting the gas to a collecting bottle.

In another embodiment of the invention the originating source consists of at least two reservoirs having different gas mixtures and/or having different anesthetic concentrations may be provided In this embodiment, a switch-over valve is provided in the line between the filter and these two reservoirs. The switch-over valve connects the line to the corresponding reservoir dependent on the gas concentration and/or composition identified in the gas analyzer. In this embodiment, for example, one reservoir may contain an extremely high concentration of an anesthetic, as is often desireable for a few minutes at the beginning of anesthesia administration, and the other reservoir may contain a lower anesthetic concentration and a higher oxygen concentration, as is needed for long-lasting anesthesia. It is also possible to have different anesthetics in the different reservoirs.

In a further embodiment of the invention at least one pressure bottle is provided as a reservoir serving as the originating source, and the compressor is disposed in the line between the filter and this reservoir. This embodiment is particularly useful if xenon is used as the anesthetic. Xenon is a very expensive inert gas, and is superior to standard anesthetics such as halothane or nitrous oxide in terms of anesthetic effect, because xenon exhibits minor side effects and completely departs from the body faster than the aforementioned anesthetics, so that patient anesthesia can be ended much sooner after the conclusion of the anesthetic administration.

In another embodiment of the invention, the filters can be redundantly employed in a known manner, with one set of filters being inserted into the line while the other set of filters is being cleaned.

DESCRIPTION OF THE DRAWINGS

The single FIGURE is a schematic diagram of an inhalation anesthesia constructed in accordance with the principles of the present invention.

DESCRIPTION OF THE PREFERRED EMBODIMENTS

In the drawing, gas lines are shown solid, and electrical lines are shown dashed.

As shown in the drawing, the inhalation anesthesia system of the present invention includes a ventilator 1, which may be, for example, a servo-ventilator such as the commercially available 900C servo-ventilator of Siemens-Elema AB. Gas from a mixer 3 is supplied to the ventilator 1 via a line 2. In the exemplary embodiment of the drawing, an oxygen pressure bottle 4 is connected to the mixer 3 via a line 5, and two pressure bottles 8 and 9 serving in combination as an originating source for anesthetic are also connected to the mixer 3 via respective lines 6 and 7. The pressure bottle 8 contains a gas mixture having a concentration of xenon less than 80% and an oxygen concentration greater than 20%. The pressure bottle 9 contains a xenon concentration greater than 80% and an oxygen concentration below 20%. Respective pressure reducing valves 10 and 11 are disposed in the lines 6 and 7 between each of the pressure bottles 8 and 9, which serve as reservoirs, and the mixer 3. The gas is supplied to a patient (not shown) by the ventilator 1 via an inspiration line 12, two gas analyzers 13 and 14, a humidifier 15, and a line 16. Exhalation gas is returned to the ventilator 1 via the gas analyzers 13 and 14 and an expiration line 17.

The exhalation gas proceeds from the ventilator 1 to a filter 20 via a line 18. A sterile filter 19 may optionally be disposed in the line 18. The filter 20 may be an absorption or adsorption filter. In the embodiment of the drawing, the filter 20 is shown as containing a specific stage for absorption of carbon dioxide, a stage for absorption of water, and a carbon filter for absorption of, for example, halothane. The filter 20 may contain a zeolite.

A zero-pressure container 21, such as an accordian bellows, is connected to the line 18. The container 21 has three electronic position sensors associated therewith, the signals of which are forwarded to a control unit 25, described in greater detail below.

A pressure sensor 26 is also connected to the line 18. The pressure sensor 26 emits a signal to the control unit 25 given the appearance of an under pressure of greater than −0.5 mbar, in the exemplary embodiment. The pressure sensor 26 may be omitted under certain conditions. For example, a valve 27 may be directly utilized for the pressure control of the compressor 28.

From the filter 20, the cleaned gas containing essentially only xenon and oxygen is returned to the originating source, i.e., to the pressure bottles 8 and 9, via the valve 27 and the compressor 28, a line 29, and three further valves 30, 31 and 32. From the last valve 32, branch lines 33 and 34 respectively lead to the bottles 8 and 9. The valve 30 is a check valve which prevents a return of the gas from the originating source to the compressor 28. An excess pressure valve 35 is connected to the line 29. A further pressure bottle 37 is provided following the valve 31 via a line 36 for use as an additional collecting vessel for contaminated gases. The collecting vessel 37 may also be used if it is necessary to temporarily switch from one anesthetic gas which is present in the originating source to a different anesthetic gas which is added from another source. This other anesthetic gas, which cannot be returned to the originating source, can be intercepted and collected in the vessel 37.

Another gas analyzer 40, which at least identifes the xenon concentration, is connected to the line 29 via a line 38 and a throttle valve 39. Preferably the gas analyzer 40 also measures the oxygen and/or carbon dioxide concentration. The gas flowing through the gas analyzer 40 is again returned to the line 18 via a line 41 having a check valve 56 therein. Removal of gas from the line 29 is limited to a minimum by the throttle valve 39.

The pressure bottle 8 is connected to a gas analyzer 48 via valves 43 and 45, and the pressure bottle 9 is connected to gas analyzer 49 via valves 42 and 44. The gas analyzers 48 and 49 respectively monitor the gas composition in the pressure bottles 8 and 9, at the least monitoring the xenon concentration therein. The gas flowing through the gas analyzers 48 and 49 is supplied via respective lines 50 and 51 to a rubber balloon 52, where the gas is collected. At suitable points in time, the gas from the balloon 52 can be returned to the line 18 via a valve 53.

A Douglas sack 55 is also connected to the line 18, via a valve 54.

The output signals of the position sensors 22 through 24, the output signals from the gas analyzers 13, 14, 40, 48 and 49, and the output signal of the under-pressure sensor 26 are all supplied to the control unit 25, as indicated by the dashed lines. All of the valves, the compressor 28, the mixer 3 and the ventilator 1 are operated by signals from the control unit 25. Additionally, the pressure bottles 8 and 9 are operated by the control unit 25.

Operation of the inhalation anesthesia equipment described above is as follows.

The desired anesthetic gas mixture is set via the control unit 25. Dependent on the desired anesthetic gas concentration, either the pressure bottle 8 or the pressure bottle 9, or both bottles 8 and 9, and possibly the pressure bottle 4 for pure oxygen, are connected to the mixer 3, where the desired mixture will be achieved. It should be noted that the mixer 3 can be omitted under certain conditions. It is also possible to connect only the pressure bottles having different anesthetic gas mixtures to the line 2 leading to the ventilator 1 alternatively or in common, and if necessary to directly connect the additional oxygen supply to the line 2.

The mixer 3 is supplied with gas quantities via valves from the originating source for anesthetic and, possibly, from the separate gas source, for example, for oxygen, these gas quantities corresponding to a prescribed gas mixture in the mixer. For example, fresh anaesthesia gas from a bottle serving as the originating source for anesthetic can be mixed with an oxygen gas in appropriate proportions or fresh anaesthesia gas mixtures having different concentrations can be mixed together from a plurality of bottles serving in combination as an originating source for anesthetic. Gases from different reservoirs and from a separate gas source such as, for example, oxygen can also be simultaneously supplied to the mixer 3. The compositions of the gas mixtures and the concentrations of the individual gases in the bottle or bottles must thus be known, this being possible, for example, via the gas analyzers 48 and 49. These values are forwarded to the control unit 25 which, based on these values and on the prescribed, desired gas composition for the gas supplied to the patient, controls the delivery of gas from the originating source of anesthetic and from the separate gas source such that the desired gas mixture is produced in the mixer 3 and is continuously maintained. The mixer 3 can also be part of the ventilator 1, for instance the bellows thereof. Appropriate valves must then be provided in the gas delivery lines 5, 6 and 7. The mixer 3 can be entirely omitted if valves are provided between the reservoirs, or the gas sources, and the ventilator 1, these valves assuming the mixer function in a certain way, i.e. delivering appropriate volumes to the ventilator 1 under the control of the control unit 1 in accord with the desired gas mixture. Further, a separate mixer 3 can be omitted if the ventilator 1 has at least two parallel inspiration systems to which the various reservoirs can be connected, and which can be driven such that the desired mixture of fresh anaesthesia gas is always maintained.

The gas mixture is supplied to the patient via the inspiration line 12. The concentration of the anesthetic, such as xenon, and/or of carbon dioxide are identified both during the inspiration phase and the expiration phase. The exhalation gas is supplied to the filter 20, via the sterile filter 19, if used, and is subsequently pressurized in the compressor 28. The zero-pressure container 21 serves as a buffer storage. The compressor 28 is started by a signal from the control unit 25 only when a defined gas volume in the container 21 is sensed by the position sensors 22 through 24.

It is also possible to continuously operate the compressor 28, and to regulate the gas flow to the compressor via the valve 27.

The under-pressure valve 26 is provided for safety reasons. If an under-pressure were to arise in the line 18, this would indicate a malfunction in the system. In response to the occurrence of such an under-pressure, the valve 27 is closed and the valve 54 is simultaneously opened, so that the exhalation air can be conducted into the Douglas sack 55. The Douglas sack 55 has a sufficiently large volume, so that the exhaled air can be collected therein for a sufficient time to permit the malfunction in the system to be located, without influencing anesthesia administration. Additionally, even in the event of such a malfunction, the expensive anesthetic gas is still collected, and can be again re-supplied from the Douglas sack 55 to the originating source for anesthetic, i.e., pressure bottles 8 or 9, via the filter 20 and the compressor 28.

The procedure for anesthesia administration is preferably begun by first rinsing the breathing passages of the patient with pure oxygen for a selected time to eliminate nitrogen and other gases (from the atmosphere) in the breathing passages. The lines of the system are simultaneously rinsed as a result thereof. The compressed gas is conducted to the additional pressure vessel 37 via the valve 31 and the line 36, or may be emptied into the environment via the valve 35. The gas analyzer 40 identifies when all nitrogen gas has been rinsed from the lines.

The patient can then be first ventilated proceeding from the pressure bottle 9 with fresh anesthesia gas having a high anesthetic concentration, for example a high xenon concentration, to achieve a sufficiently deep anesthesia as quickly as possible. The gas cleaned by the filter 20 is again monitored for xenon concentration by the gas analyzer 40, and may also be checked for other gas concentrations. Because the patient initially absorbs a large quantity of xenon, an increased oxygen concentration will be present in the exhaled gas. This concentration decreases extremely quickly, and falls below the value of the oxygen concentration in the fresh anesthesia gas in the stable, ultimate condition of anesthesia. If, for example, a fresh gas mixture of 80% xenon and 20% oxygen is selected for a defined depth of anesthesia, a part of the oxygen is used by the patient, so that the concentration of the oxygen falls below 20% in the exhalation gas. If, for example, this concentration is re-supplied to a bottle, the xenon consumption therein rises slightly above 80% in the ultimate anesthesia condition. In the steady state, the patient can be constantly directly ventilated from the originating source for anesthesia, with the quantity of consumed oxygen added from a separate gas source with each breath. The valve 31 is switched so that the compressed gas is returned through this valve and the valve 32 either to the pressure bottle 8 or the pressure bottle 9 via one of the lines 33 or 34, dependent on the measured concentration.

As is known, the anesthetic consumption of the patient rapidly decreases when a defined depth of anesthesia is reached. If ventilation is initially undertaken with pure xenon, i.e., if one of the bottles contains pure xenon, a switch to the other pressure bottle having a fresh anesthetic gas mixture with only a slight anesthetic concentration can be undertaken. This can be accomplished, for example, by the control unit 25 after the intended depth of anesthesia has been reached. It is then sufficient for further anesthesia to re-supply a significantly smaller quantity of anesthetic. The control unit 25 can therefore switch to the pressure bottle, such as the bottle 8, having a fresh anesthetic gas mixture with a lower anesthetic concentration for this phase. The gas composition in the pressure bottles 8 and 9 is constantly monitored by the gas analyzers 48 and 49. The corresponding values are forwarded to the control unit 25. The xenon consumption of the patient can be exactly calculated form these values, together with the supplied volume of fresh anesthetic gas and, for example, from the xenon content of the exhaled gas identified by the gas analyzer 14. A value corresponding to this consumption is a useful control parameter for identifying the depth of anesthesia.

Only two pressure bottles 8 and 9 for different gas mixtures have been shown in the exemplary embodiment. It is possible to use more than two pressure bottles as the originating source of anesthesia in the context of the present invention. It is also possible to provide two filters in parallel, instead of the single filter 20. These two filters are connected in a known manner for alternating operation, so that one filter can always be actively used for cleaning the exhaled gas, while the other filter is being cleaned.

The control unit 25 may, for example, be a microprocessor.

Although modifications and changes may be suggested by those skilled in the art it is the intention of the inventors to embody within the patent warranted hereon all changes and modifications as reasonably and properly come within the scope of their contribution to the art.

We claim as our invention:

1. A system for administering anesthesia to a patient by inhalation through the breathing passages of said patient, said system comprising:
    an originating pressurized source for an anesthetic;
    a ventilator means for supplying said anesthetic from said originating source to said breathing passages of said patient including an inspiration line and an expiration line, said expiration line being separate from said originating source; and
    means for returning gas from said expiration line into said originating source through at least one filter which filters predetermined gas components out of said gas from said expiration line.

2. A system as claimed in claim 1, wherein said originating source contains anesthetic in at least an amount necessary for anesthetizing said patient for a time period during which said patient is to be kept under anesthesia.

3. A system as claimed in claim 1, further comprising at least a further source of one additional gas, and means for mixing said anesthetic from said source with said at least one additional gas before supplying said at least one additional gas mixed with said anesthetic to said ventilator.

4. A system as claimed in claim 3, wherein said source of at least one additional gas is a source of oxygen.

5. A system as claimed in claim 1, wherein said originating source contains a gas which is a mixture of said anesthetic and another gas.

6. A system as claimed in claim 5, wherein said another gas is oxygen.

7. A system as claimed in claim 1, wherein said originating source comprises two containers having respectively different gas compositions, and further comprising:
    a gas line leading from an output of said filter to each of said containers;
    gas analyzer means disposed in said gas line for measuring the gas composition at said output of said filter;
    a valve disposed in said gas line which connects one of said containers at a time to said output of said filter; and
    control means responsive to a signal from said gas analyzer means for switching said valve to connect one of said containers to said output of said filter dependent on said gas composition at said output.

8. A system as claimed in claim 1, wherein said originating source comprises two containers having respectively different anesthetic concentrations, and further comprising:
    a gas line leading from an output of said filter to each of said containers;
    gas analyzer means disposed in said gas line for measuring the anesthetic concentrations at said output of said filter;
    a valve disposed in said gas line which connects one of said containers at a time to said output of said filter; and
    control means responsive to a signal from said gas analyzer means for switching said valve to connect one of said containers to said output of said filter dependent on said anesthetic concentration at said output.

9. A system as claimed in claim 8, wherein one of said containers has an anesthetic concentration therein selected for obtaining a desired depth of anesthesia of said patient.

10. A system as claimed in claim 8, wherein one of said containers has an anesthetic concentration greater than 80% and the other of said containers has an anesthetic concentration less than 80%.

11. A system as claimed in claim 1, wherein said gas in said originating source is at a pressure higher than atmospheric pressure, and further comprising a compressor means connected between said filter and said originating source for pressurizing the gas returned to said originating source.

12. A system as claimed in claim 11, wherein said originating source consists of at least one pressure bottle.

13. A system as claimed in claim 1, further comprising gas analyzer means for monitoring the concentration of anesthetic gas in said originating source.

14. A system as claimed in claim 1, further comprising:
   a gas line communicating said expiration line with said filter;
   a zero pressure container connected to said gas line;
   means for monitoring the amount of gas from said gas line collected in said zero pressure contained;
   a compressor disposed between an output of said filter and said originating source; and
   means responsive to said means for monitoring for starting said compressor upon collection of a selected amount of gas in said zero-pressure container.

15. A system as claimed in claim 14, wherein said zero pressure container is a bellows, and wherein said means for monitoring is a plurality of position sensors which generate respective signals corresponding to the amount of expansion of said bellows.

16. A system as claimed in claim 1, further comprising:
   a gas line communicating said expiration line with an input of said filter;
   a zero pressure container connected to said gas line;
   means for monitoring the amount of gas from said gas line collected in said zero pressure container;
   a valve disposed between an output of said filter and said originating source; and
   means responsive to said means for monitoring for controlling said value dependent on the amount of gas collected in said zero pressure container.

17. A system as claimed in claim 16, wherein said zero pressure container is a bellows, and wherein said means for monitoring is a plurality of position sensors which generate respective signals corresponding to the amount of expansion of said bellows.

18. A system as claimed in claim 1, further comprising:
   a gas line connecting an output of said filter with said originating source;
   means for monitoring the pressure of gas in said gas line; and
   means for discharging a selected amount of said gas in said gas line to the atmosphere if the pressure of said gas in said gas line exceeds a predetermined amount.

19. A system as claimed in claim 1, further comprising:
   a gas line connecting an output of said filter with said originating source;
   a collecting vessel; and
   means for selectively diverting gas in said gas line to said collecting vessel instead of supplying said gas to said originating source.

20. A system as claimed in claim 1, wherein said originating source contains xenon.

21. A system as claimed in claim 1, wherein said filter includes a zeolite.

22. A system as claimed in claim 1, further comprising:
   means for monitoring a gas characteristic at at least one location in said system and generating a signal corresponding to said characteristic;
   a line containing a valve connecting said filter to said reservoir; and
   control means responsive to said signal from said means for monitoring for operating said valve dependent on the monitored characteristic of said gas.

23. A system as claimed in claim 22, wherein said means for monitoring is a means for monitoring the gas composition at at least one location in said system.

24. A system as claimed in claim 22, wherein said means for monitoring is a means for monitoring the gas concentration at at least one location in said system.

25. A system for administrating anesthetic to the breathing passages of a patient comprising:
   an originating pressurized source containing anesthetic;
   a source of at least one additional gas;
   means for mixing said anesthetic and said additional gas;
   a ventilator having an input connected to an output of said means for mixing;
   means communicating an output of said ventilator with said breathing passages of said patient for supplying a gas mixture from said means for mixing to said patient, said means for supplying including an inspiration line and an expiration line,;
   means for returning exhaled gas from said patient into said originating source for storage in said source, said means for returning connecting said expiration line to said originating source; and
   at least one filter means for removing selected gases from said exhalation gas disposed in said means for returning.

26. A system for administering anesthetic to the breathing passages of a patient comprising:
   an originating source having a plurality of containers each containing gas therein of a different characteristic;
   a ventilator;
   means for connecting at least one of said plurality of containers to an input of said ventilator;
   means for communicating said ventilator with the breathing passages of said patient including an inspiration line and an expiration line;
   a return line connecting said expiration line to said originating source for returning exhaled gas from said patient to said originating source;
   at least one filter means in said return line for removing selected gas components from said exhaled gas before said exhaled gas is returned to said originating source;
   a compressor disposed in said return line;
   a switch-over valve disposed in said return line after said compressor which selectively diverts said exhaled gas from said return line to one of said plurality of containers in said originating source;

monitoring means connected to said return line between said expiration line and said compressor for measuring the pressure of the gas in said return line ahead of said compressor and generating an electrical signal corresponding thereto;

gas analyzer means connected to said return line between said compressor and said switch-over valve for monitoring a characteristic of the gas in the return line after said compressor and generating an electrical signal thereto; and control means responsive to said signal from said monitoring means to control operation of said compressor and responsive to said signal from said gas analyzer means to control operation of said switch-over valve.

27. A method for administering anesthetic gas to the breathing passages of a patient comprising the steps of:

drawing anesthetic gas from an originating pressurized source to a ventilator connected to the breathing passages of said patient;

ventilating the patient with anesthetic gas by said ventilator via an inspiration line and an expiration line;

filtering selected gas components from exhaled gas from said patient from said expiration line to obtain filtered gas;

returning the filtered gas into said originating source; and storing the filtered gas in said originating source for reuse.

* * * * *